(12) United States Patent
Lee

(10) Patent No.: US 8,215,955 B2
(45) Date of Patent: Jul. 10, 2012

(54) ENDODONTIC INSTRUMENT FOR ROOT CANAL FILLING AND HEATING TIP ADAPTED TO THE SAME

(75) Inventor: In-Whan Lee, Gunpo-si (KR)

(73) Assignee: BNL Biotech Co., Ltd., Gyeonggi-do (KR)

( * ) Notice: Subject to any disclaimer, the term of this patent is extended or adjusted under 35 U.S.C. 154(b) by 186 days.

(21) Appl. No.: 12/446,301

(22) PCT Filed: Oct. 18, 2007

(86) PCT No.: PCT/KR2007/005103
§ 371 (c)(1),
(2), (4) Date: Sep. 22, 2009

(87) PCT Pub. No.: WO2008/048054
PCT Pub. Date: Apr. 24, 2008

(65) Prior Publication Data
US 2010/0297571 A1  Nov. 25, 2010

(30) Foreign Application Priority Data

Oct. 18, 2006 (KR) .................. 10-2006-0101541
Nov. 10, 2006 (KR) .................. 10-2006-0111242

(51) Int. Cl.
*A61C 3/00* (2006.01)
(52) U.S. Cl. ............................................. 433/32
(58) Field of Classification Search .......... 433/25, 433/27, 29, 31–32, 34, 50–53, 59, 74, 75, 433/80–90, 102, 114, 118, 119, 120, 122–124, 433/141, 146–147, 224; 374/179; 136/230, 136/235, 219; 272/326, 333, 638, 639, 63, 272/52, 146.1, 146.2, 146.5; 406/154, 155; 362/573

See application file for complete search history.

(56) References Cited

U.S. PATENT DOCUMENTS

| 3,919,775 | A | | 11/1975 | Malmin |
| 4,353,698 | A | * | 10/1982 | McSpadden .................. 433/164 |
| 5,393,350 | A | * | 2/1995 | Schroeder ..................... 136/205 |
| 5,495,093 | A | * | 2/1996 | Griffith ........................ 219/497 |
| 5,752,825 | A | | 5/1998 | Buchanan |
| 5,893,713 | A | * | 4/1999 | Garman et al. ................. 433/32 |
| 6,285,010 | B1 | * | 9/2001 | Fujikawa et al. ............. 219/411 |
| 6,910,887 | B2 | * | 6/2005 | Van Den Houdt ............. 433/32 |
| 6,981,868 | B2 | * | 1/2006 | Okawa et al. .................. 433/81 |

FOREIGN PATENT DOCUMENTS

KR 1020040006371 A 1/2004

* cited by examiner

*Primary Examiner* — Cris L Rodriguez
*Assistant Examiner* — Mirayda A Aponte
(74) *Attorney, Agent, or Firm* — IP & T Group LLP

(57) ABSTRACT

An endodontic instrument for root canal filling includes a body having DC power source and printed circuit board, a heating tip connected to the body, a switch, and a control circuit for switching on/off power supply to the heating tip. The heating tip includes a first metal part serving as a resistant tube, a second metal part disposed inside the first metal part and configured to supply power, check a thermoelectric power (+) terminal, a third metal part disposed inside the first metal part and configured to supply power, a contact part, an insulator disposed inside the first metal part and enclosing surfaces of the second and third metal parts, first conductive tube, a second conductive tube; and an insulator connected and fixed to the first and second conductive tubes, where temperature is detected using thermoelectric power of the thermocouple.

6 Claims, 6 Drawing Sheets

ENDODONTIC INSTRUMENT FOR ROOT CANAL FILLING AND HEATING TIP ADAPTED TO THE SAME

This application is a national stage application of PCT/KR2007/005103 filed on Oct. 18, 2007, which claims priority of Korean patent application number 10-2006-0101541 filed on Oct. 18, 2006 and Korean patent application number 10-2006-0111242 filed on Nov. 10, 2006. The disclosure of each of the foregoing applications is incorporated herein by reference in its entirety.

TECHNICAL FIELD

The present invention relates to an endodontic instrument for root canal filling and a heating tip adapted to the same. In particular, the endodontic instrument for root canal filling includes: a body having a direct current (DC) power source and a printed circuit board; a heating tip connected to the body and including a first metal part serving as a resistant tube, a second metal part and a third metal part forming a thermocouple, and an insulator enclosing the second metal part and the third metal part; a switch for operating the heating tip; and a control circuit for switching on/off the power supply applied to the heating tip.

BACKGROUND ART

In a decayed tooth treating method, which is generally used in a dental clinic, a decayed portion of a tooth is first removed with drilling. When the pulp of the tooth is injured, the injured or affected pulp is also removed using an endodontic file. After the root canal has been prepared, the root canal is sealed with root canal filling materials. Finally, a prosthetic treatment is carried out on the tooth. In the root canal filling procedure, gutta-percha cones are used as a permanent filling material having an auxiliary function for enabling the filler, which is endodontic cement or a sealer, to penetrate into the root canal and thus to seal up the root canal. Gutta-percha, which is a natural vegetable extract, has a solid phase at room temperature, but has the form of a semisolid gum when it is compressed or heated. The gutta-percha having the form of such a solid gum for the root canal filling, is called "gutta-percha cone".

Generally, gutta-percha cones are prepared by adding zinc oxide, barium sulfate, wax, and pigment to gutta-percha, kneading them into a paste in a mixer, extruding the paste in the form of a sheet using rollers, cutting the sheet into pieces, and shaping the pieces into a conical structure. Thus, gutta-percha cones having various sizes can be formed. The gutta-percha cone is widely used as a material for endodontic treatment because it is known to be most biologically compatible with living bodies and it is harmless to the root apexes of teeth. Gutta-percha cones, which are currently commercially available, are classified into a standardized cone and an accessory cone. The standardized cone has a shape identical to that of a dental file.

In endodontic treatment for a decayed tooth, the affected pulp of the tooth is first drilled to remove affected nerve tissues. After the root canal has been prepared, the root canal is sealed with root canal filling materials. For the root canal filling, a gutta-percha cone having a suitable size is then inserted into the root canal to fix with the filler, which is endodontic cement or a sealer, to the main and accessory portions of the root canal. Thereafter, a filler is coated on the root canal wall. In this case, it is important to bring the gutta-percha cone into complete contact with the root canal wall and apical area of the tooth in order to prevent the root canal from being further affected by a source of infected area.

After completion of the root canal filling procedure, the filling state in the root canal is confirmed using X-ray photography. The gutta-percha cone is then removed. For the removal of the gutta-percha cone, an excavator, an endodontic plugger, or a spreader is used in a state of being heated in flame.

Generally, the endodontic instrument for root canal filling includes a handpiece, and a control box which includes a power source for supplying electric power to the handpiece, and a controller for controlling the handpiece. The handpiece, which is grasped by a doctor for endodontic treatment, is separate from the control box and it is electrically connected with the control box by a cable.

Hereinafter, a conventional endodontic instrument for root canal filling will be described with reference to FIGS. 1 and 2.

FIG. 1 is a perspective view of a conventional endodontic instrument for root canal filling, and FIG. 2 is a sectional view of a heating tip in the conventional endodontic instrument for root canal filling illustrated in FIG. 1. Referring to FIGS. 1 and 2, the conventional endodontic filling instrument 100 includes a heating tip 110, a handpiece 120, a cable 130, and a control box 140. The control box 140 includes a power switch 142, a control panel 141, and a display (not shown) for displaying an operation state of the filling instrument 100. The handpiece 120 is connected to the heating tip 110 for supplying heat to gutta-percha to melt or cut the gutta-percha. The handpiece 120 and the control box 140 are connected to each other by the cable 130. Electric power required by the handpiece 120 is supplied from the control box 140 via the cable 30.

The heating tip 110 includes a heat generating core 114, an insulating film 112 enclosing the heat generating core 114, and a conical resistant heat generating layer 111 having a cross-sectional area gradually reduced toward a front end 113 of the heat generating core 114. The front end 113 of the heat generating core 114 is connected to the resistant heat generating layer 111 because it is not enclosed by the insulating film 112.

Accordingly, when a current flows through the resistant heat generating layer 111 and the heat generating core 114, a current density increases at the front end 113 where the heat generating core 114 and the resistant heat generating layer 111 are connected to each other, thus generating more heat than any portion.

However, the above-mentioned conventional filling instrument has a problem in that there is inconvenience in carrying the filling instrument because the control box and the handpiece are separate from each other. Further, the heating tip has poor heating efficiency.

DISCLOSURE

Technical Problem

An embodiment of the present invention is directed to providing an endodontic filling instrument having excellent heat generation efficiency. Specifically, the endodontic instrument for root canal filling includes a heating tip having a first metal part, a second metal part, and a third metal part. The first metal part is a resistant tube. The second metal part supplies electric power, checks a thermoelectric power (+) terminal, and serves as a (+) terminal of the thermocouple. The third metal part supplies electric power and serves as a (−) terminal of the thermocouple. The second metal part and the third metal part contact each other at a position spaced apart from an end of the heating tip by a predetermined distance. A thermoelectric power is generated at the contact part. Accordingly, endodontic filling instrument can detect temperature using the thermoelectric power of the thermocouple of the second and third metal parts.

Other objects and advantages of the present invention can be understood by the following description, and become apparent with reference to the embodiments of the present invention. Also, it is obvious to those skilled in the art of the present invention that the objects and advantages of the present invention can be realized by the means as claimed and combinations thereof.

Technical Solution

In accordance with an aspect of the present invention, there is provided an endodontic instrument for root canal filling, which includes: a body including a DC power source and a printed circuit board; a heating tip connected to the body, the heating tip including a first metal part serving as a resistant tube, a second metal part and a third metal part forming a thermocouple, and an insulator enclosing the second metal part and the third metal part; a switch for operating the heating tip; and a control circuit for switching on/off the supply of a voltage applied to the heating tip.

In accordance with another aspect of the present invention, there is provided a heating tip of an endodontic instrument for root canal filling, which includes: a first metal part serving as a resistant tube; a second metal part disposed inside the first metal part, formed of a material having a small electric resistance, and configured to supply electric power, check a thermoelectric power (+) terminal, and serve as a (+) terminal of a thermocouple; a third metal part disposed inside the first metal part, and configured to supply electric power and serve as a (−) terminal of the thermocouple; a contact part in which one end of the second metal part and the third metal part contact each other; an insulator disposed inside the first metal part and enclosing surfaces of the second metal part and the third metal part; a first conductive tube contacting the other end of the second metal part; a second conductive tube contacting the other end of the third metal part; and an insulator connected and fixed to the first and second conductive tubes, whereby temperature is detected using the thermoelectric power of the thermocouple of the second and third metal parts.

Advantageous Effects

The embodiments of the present invention provide an endodontic instrument for root canal filling, which has excellent heat generation, and a heating tip adapted to the same. The endodontic instrument for root canal filling includes: a heating tip having a first metal part serving as a resistant tube, a second metal part and a third metal part forming a thermocouple, and an insulator enclosing the second metal part and the third metal part; and a control circuit for switching on/off the power supply applied to the heating tip. Further, a heating tip of an endodontic instrument for root canal filling includes: a first metal part serving as a resistant tube; a second metal part disposed inside the first metal part, formed of a metal having low electric resistance, and configured to supply electric power, check a thermoelectric power (+) terminal, and serve as a (+) terminal of a thermocouple; a third metal part disposed inside the first metal part, and configured to supply electric power and serve as a (−) terminal of the thermocouple; a contact part in which one end of the second metal part and the third metal part contact each other; an insulator disposed inside the first metal part and enclosing surfaces of the second metal part and the third metal part; a first conductive tube contacting the other end of the second metal part; a second conductive tube contacting the other end of the third metal part; and an insulator connected and fixed to the first and second conductive tubes. Accordingly, the heating tip can detect temperature using a thermoelectric power of the thermocouple of the second and third metal parts.

BEST MODE FOR THE INVENTION

The advantages, features and aspects of the invention will become apparent from the following description of the embodiments with reference to the accompanying drawings, which is set forth hereinafter.

Hereinafter, the configuration, function and effect of an endodontic instrument for root canal filling in accordance with the embodiments of the present invention will be described below with reference to FIGS. 3 to 5.

Figure 1:
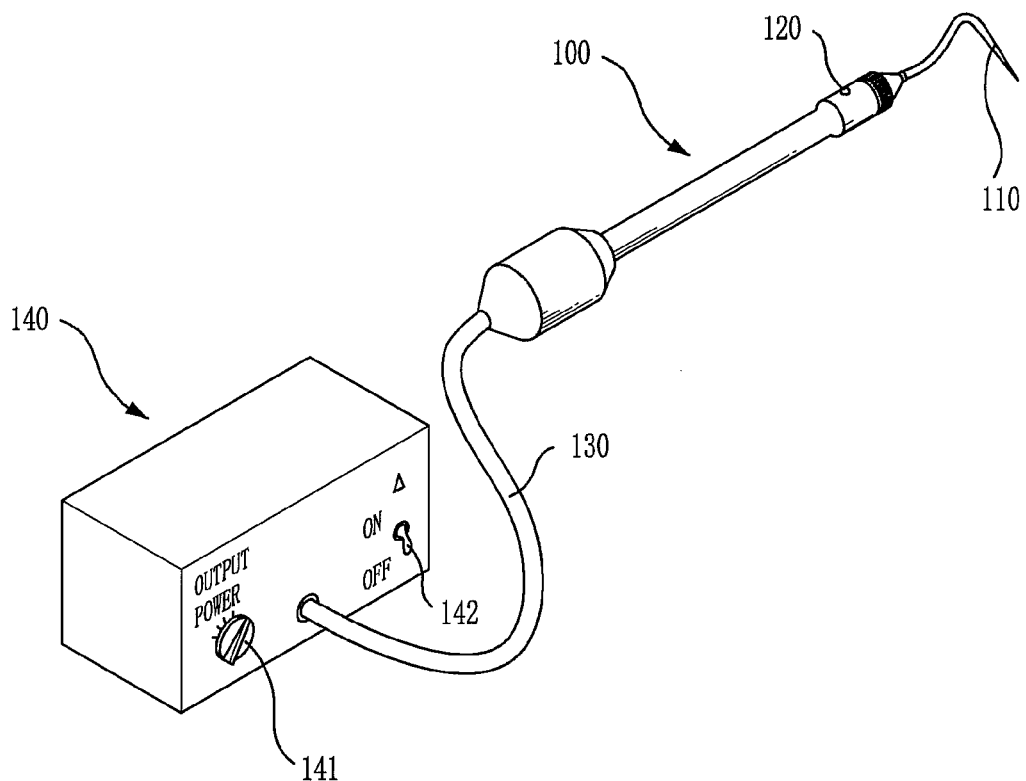
FIG. 1 is a perspective view of a conventional endodontic instrument for root canal filling.
Figure 2:
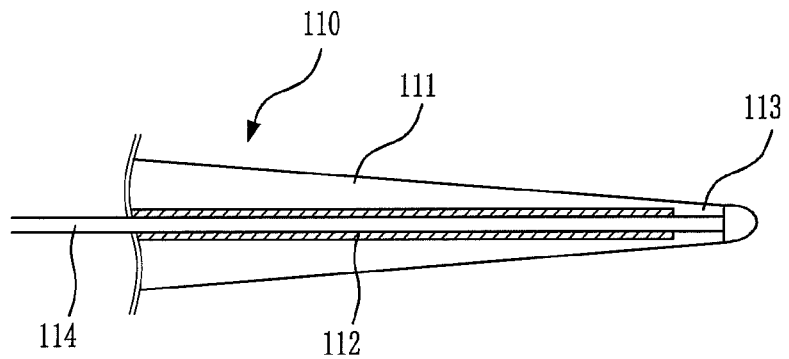
FIG. 2 is a sectional view of a heating tip in the conventional endodontic instrument for root canal filling illustrated in FIG. 1.
Figure 3:
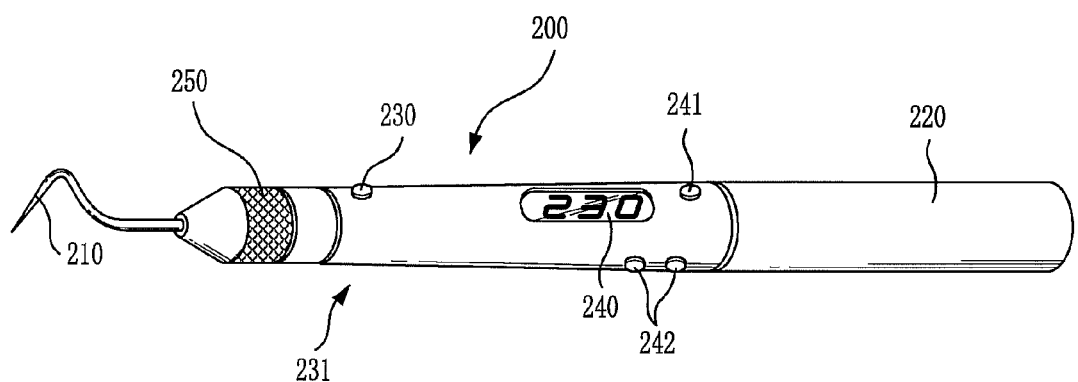
FIG. 3 is a perspective view of an endodontic instrument for root canal filling in accordance with an embodiment of the present invention.

FIG. 3 is a perspective view of an endodontic instrument for root canal filling in accordance with an embodiment of the present invention. Referring to FIG. 3, the endodontic filling instrument 200 has a pen-shaped body 220 so that an operator can easily grasp it. In addition, the endodontic filling instrument 200 includes a heating tip 210, a switch 230, a display 240, and a light emitter 250. The body 220 includes a DC power source and a main printed circuit board arranged therein.

The heating tip 210 extends forwardly from the body 220 and generates heat to melt gutta-percha disposed at a desired position and thus fill a root canal with the melt gutta-percha. The display 240 displays an operation state of the heating tip 210 and is manipulated using an operation condition setting button 241, e.g., a power switch or temperature control switch.

The heating tip 210 is operated using the switches 230 and 231. Further, the light emitter 250 may be installed on a front end portion of the body 220 to illuminate an affected part to be treated. A battery charging terminal 242 is formed in the body 220.

Figure 4:
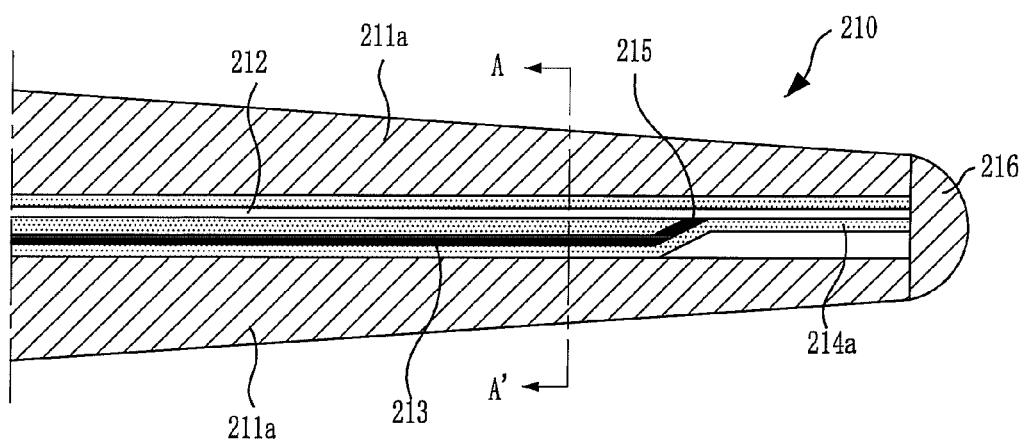
FIG. 4 is a partial sectional view illustrating a front end of a heating tip in FIG. 3 in accordance with an embodiment of the present invention.
Figure 6:
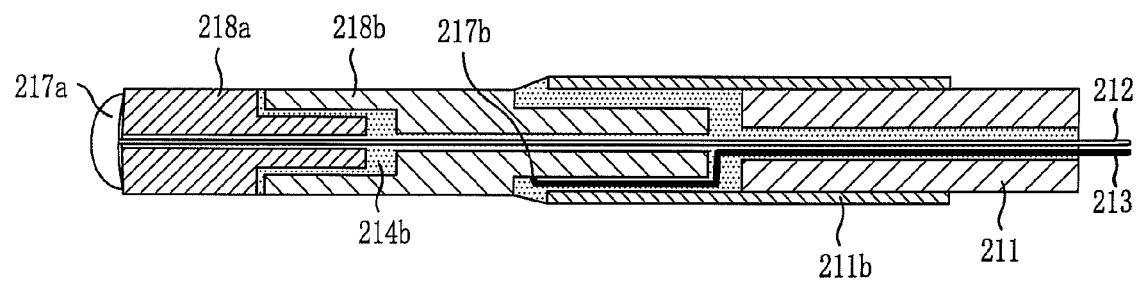
FIG. 6 is a sectional view illustrating a rear end of a heating tip in FIG. 3.
Figure 7:
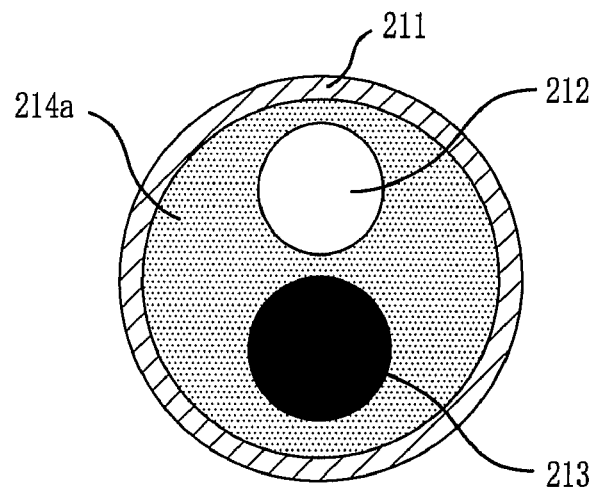
FIG. 7 is a sectional view taken along line A-A' of FIG. 4 in accordance with an embodiment of the present invention.
Figure 8:
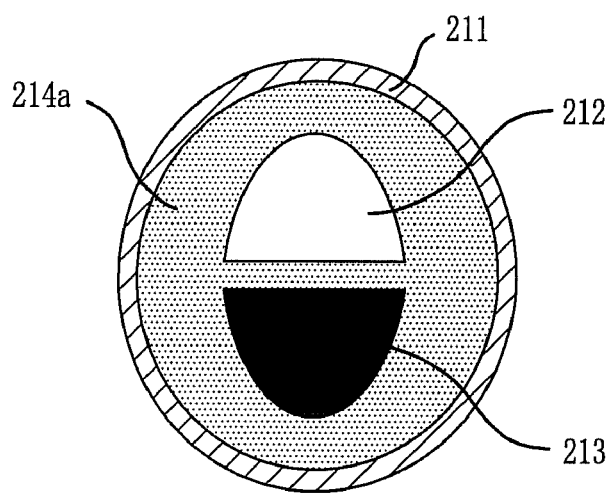
FIG. 8 is a sectional view taken along line A-A' of FIG. 4 in accordance with another embodiment of the present invention.

FIG. 4 is a sectional view illustrating the front end of the heating tip in FIG. 3 in accordance with an embodiment of the present invention. FIG. 5 is a sectional view illustrating the front end of the heating tip in FIG. 3 in accordance with another embodiment of the present invention. FIG. 6 is a sectional view illustrating the rear end of the heating tip in FIG. 3. FIG. 7 is a sectional view taken along line A-A' of FIG. 4 in accordance with an embodiment of the present invention. FIG. 8 is a sectional view taken along line A-A' of FIG. 4 in accordance with another embodiment of the present invention.

Referring to FIG. 4, the heating tip 210 includes a first metal part 211a, a second metal part 212, a third metal part 213, and an insulator 214.

The first metal part 211a is a resistant tube and is formed of any one selected from the group consisting of nickel, nickel alloy, titanium alloy and a combination thereof. The second metal part 212 is disposed inside the first metal part 211a. The second metal part 212 supplies electric power, checks a thermoelectric power (+) terminal, serves as a (+) terminal of a thermocouple, and is formed of a metal having low electric resistance, e.g., copper, copper alloy, silver alloy or a combination thereof. The third metal part 213 is disposed inside the first metal part 211a. The third metal part 213 supplies electric power and serves as a (−) terminal of the thermocouple. The third metal part 213 is formed of nickel or nickel alloy.

When the sectional areas of the second metal part 212 and the third metal part 213 increase and electric power is supplied thereto, the resistance is small and the second metal part 212 and the third metal part 213 generate low heat. Further, high heat is generated from the surface of the first metal part 211a and a coating of the insulator is protected.

The insulator 214a is disposed inside the first metal part 211a and encloses the second metal part 212 and the third metal part 213. The insulator 214a is formed of ceramic epoxy or enamel. The second metal part 212 and the third metal part 213 may form a contact part 215, i.e., a thermocouple junction, at a position spaced apart from the end 216 of the heating tip 210 by a predetermined distance. The contact part 215, i.e., the thermocouple junction, may be formed at the end 216 of the heating tip 210 to generate a thermoelectric power. Further, the contact part 215 may be formed at a position located 0.5-1.0 mm inwardly from the end of the heating tip by a spot or the like. The first metal part 211a may have a tapered shape with a thickness of 0.5 to 1.0 mm. Further, the third metal part 213 and the first metal part 211a contact each other at the end of the heating tip 210.

Figure 5:
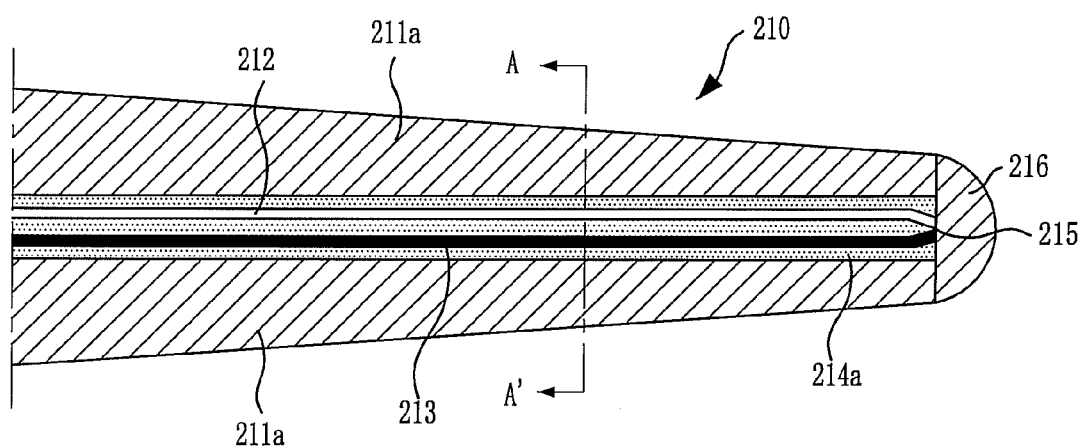
FIG. 5 is a partial sectional view illustrating a front end of a heating tip in FIG. 3 in accordance with another embodiment of the present invention.

Referring to FIG. 5, the second metal part 212 and the third metal part 213 may contact each other at the end of the heating tip 210.

Referring to FIG. 6, first and second conductive tubes 218a and 218b are disposed at a rear end of the heating tip 210. The second metal part 212 contacts the first conductive tube 218a to form a thermocouple terminal 217a. The thermocouple terminal 217a may be formed by a spot or soldering.

The third metal part 213 contacts the second conductive tube 218b to form a thermocouple terminal 217b. The thermocouple terminal 217b may be formed by a spot or soldering. The first and second conductive tubes 218a and 218b are connected and fixed to the insulator 214b in a straight line. The first metal part 211b may be further provided at the rear end of the heating tip 210 in order to generate heat at a portion where a large amount of electric power is supplied.

Referring to FIGS. 7 and 8, the second metal part 212 and the third metal part 213 disposed inside the first metal part 211 may have cross-sections of semicircular or circular shapes facing each other. The insulator 214a insulates the first metal part 211a, the second metal part 212, and the third metal part 213 from contacting one another.

Figure 9:
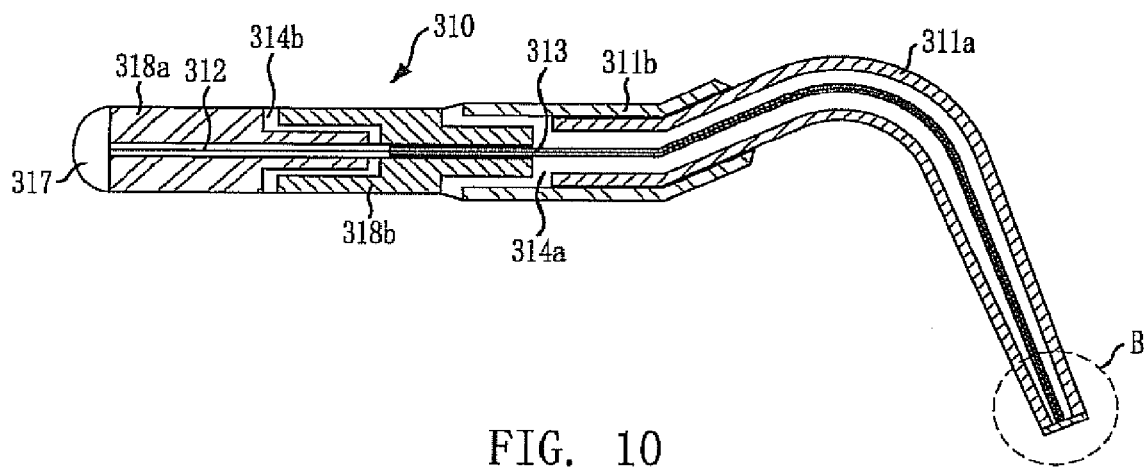
FIG. 9 is a sectional view of an endodontic instrument for root canal filling in accordance with another embodiment of the present invention.
Figure 10:
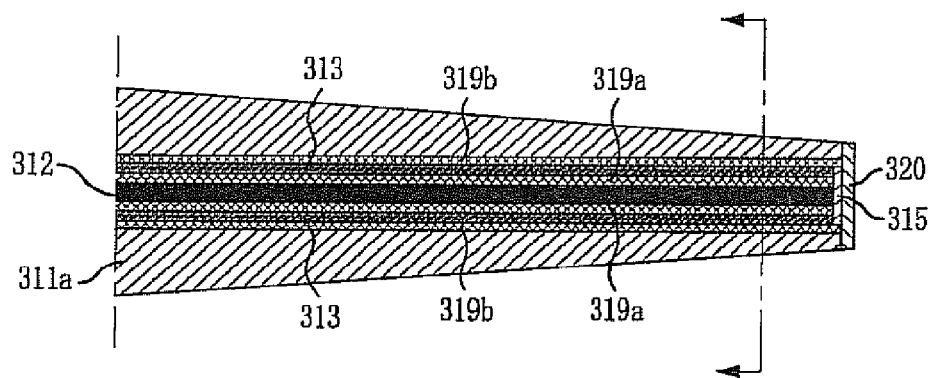
FIG. 10 is a detailed sectional view of an end portion (B) of a heating tip illustrated in FIG. 9.

FIG. 9 is a sectional view of an endodontic instrument for root canal filling in accordance with another embodiment of the present invention, and FIG. 10 is a detailed sectional view of an end portion (B) of a heating tip illustrated in FIG. 9. Referring to FIGS. 5 and 10, the heating tip 310 includes first metal parts 311a and 311b, a second metal part 312, a third metal part 313, a thermocouple junction 315, first and second conductive tubes 318a and 318b, and insulators 314a, 314b, 319a and 319b.

The first metal parts 311a and 311b are resistant tubes. The first metal part 311a may be formed of nickel alloy. The third metal part 313 is provided in a tube type and disposed inside the first metal part. The third metal part 313 supplies electric power and serves a (−) terminal of a thermocouple.

The third metal part 313 may be formed of nickel or nickel alloy. The second metal part 312 is provided in a wire type and disposed inside the third metal part 313. The second metal part 312 supplies electric power, checks a thermoelectric power (+) terminal, and serves as a (+) terminal of the thermocouple. The second metal part 312 may be formed of copper or copper alloy.

Figure 11:
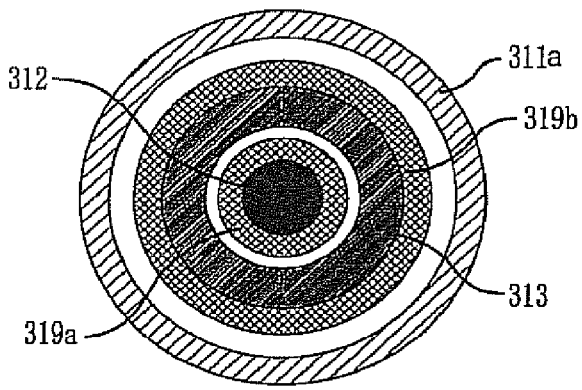
FIG. 11 is a sectional view of the heating tip, taken along line A-A' of FIG. 10.

FIG. 11 is a sectional view of the heating tip, taken along line A-A' of FIG. 10. Referring to FIG. 11, an insulator 319a, which is a ceramic epoxy, is disposed around a periphery of the wire-type second metal part 312, and a insulator 319b is disposed around a periphery of the third metal part 313.

A thermocouple junction where the end of the second metal part 312 and the end of the third metal part 313 contact each other is formed in an end portion 320 of the heating tip. A heating power is checked through the thermocouple junction.

In addition, the first conductive tube 318a serves as a terminal contacting the second metal part 312. The first conductive tube 318a and the second metal part 312 contact each other by the thermocouple terminal 317. The second conductive tube 318b serves as a terminal contacting the third metal part 313.

The heating tips 210 and 310 in accordance with the embodiments of the present invention may be formed in a curved shape, such as an L-shape, as illustrated in FIGS. 3 and 9.

Figure 12:
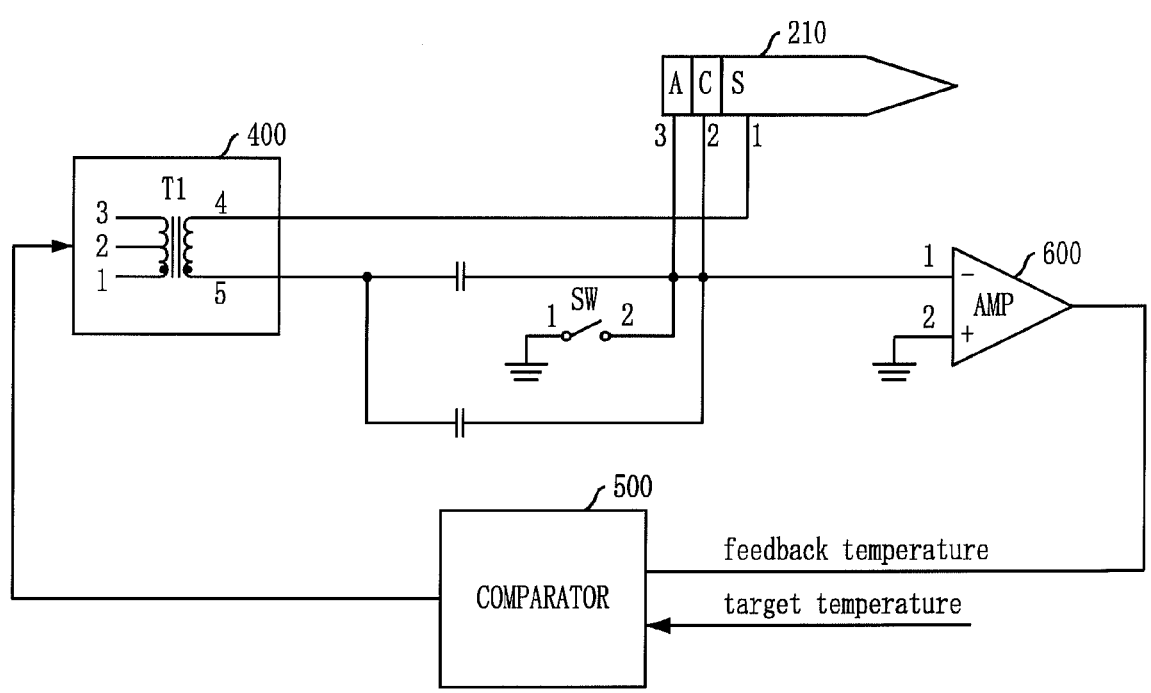
FIG. 12 is a circuit diagram of a control circuit for controlling heating and temperature measurement in a heating tip of the endodontic instrument for root canal filling.

FIG. 12 is a circuit diagram of a control circuit for controlling the heating and the temperature measurement in the heating tip of the endodontic instrument for root canal filling. Referring to FIG. 12, the control circuit includes a heater, a switch SW, a heater driver 400, an amplifier 600, and a comparator 500. The heater includes a resistant tube wire 1(S) serving as the first metal part of the heating tip, a thermocouple wire 3(A) serving as the second metal part, and a conductive wire 2(C) serving as the third metal part.

The switch SW switches on/off the electric power supply to the heating tip. The heater driver 400 supplies the electric power to the heating tip. The amplifier 600 amplifies a slight voltage generated from the contact part of the heating tip. The comparator 500 compares the amplified voltage with a set temperature.

The heating of the heating tip is performed by switching off the switch SW and applying an alternating current (AC) voltage to one terminal comprised of the thermocouple wire 3(A) and the conductive wire 2(C), and another terminal comprised of the resistant tube wire 1(S). In this case, heat is generated at the contact part 215 of the heating tip and the end of the first metal part. After a predetermined time elapses, the supply of the voltage applied to the heater driver 400 is stopped and the switch SW is then turned on.

Due to the voltage that has been already applied, the temperature around the end of the heating tip is increased. A small voltage is generated from the contact part 215 by the thermoelectric power. The small voltage is transferred through the amplifier 600 to the comparator 500 and is compared with the set temperature. A voltage is applied to the heater driver 400 and the temperature is again measured. By repeating these procedures, the current is adjusted such that the heating tip reaches the set temperature.

The present application contains subject matter related to Korean Patent Application Nos. 10-2006-0101541 and 10-2006-0111242, filed in the Korean Intellectual Property Office on Oct. 18, 2006, and Nov. 10, 2006, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

What is claimed is:

1. An endodontic instrument for root canal filling, comprising:
    a body including a direct current (DC) power source and a printed circuit board;
    a heating tip connected to the body;
    a switch for operating the heating tip; and
    a control circuit for switching on/off power supply applied to the heating tip,
    wherein the heating tip includes:
        a first metal part serving as a resistant tube;
        a third metal part provided in a tube type and disposed inside the first metal part and configured to supply thermoelectric power and serve as a (−) terminal of a thermocouple;
        a second metal part disposed inside the third metal part in a form of wire and configured to supply the thermoelectric power, check a thermoelectric power (+) terminal, and serve as a (+) terminal of the thermocouple;
        a thermocouple junction in which one end of the second metal part and one end of the third metal part contact each other;
        a first insulator disposed inside the first metal part and enclosing a surface of the third metal part;
        a second insulator disposed inside the third metal part and enclosing a surface of the second metal part;
        a first conductive tube contacting the other end of the second metal part;
        a second conductive tube contacting the other end of the third metal part; and
        a third insulator connected and fixed to the first and second conductive tubes, wherein temperature is detected using the thermoelectric power of the thermocouple of the second and third metal parts.

2. The endodontic filling instrument of claim 1, wherein the second metal part supplies electric power, checks a thermoelectric power (+) terminal, and serves as a (+) terminal of the thermocouple, and the third metal part supplies electric power, and serves as a (−) terminal of the thermocouple.

3. The endodontic filling instrument of claim 1, wherein the first metal part is formed of any one selected from the group consisting of nickel, nickel alloy, titanium alloy and a combination thereof;
    the second metal part is formed of any one selected from the group consisting of copper, copper alloy, silver alloy and a combination thereof;
    the third metal part is formed of nickel or nickel alloy; and
    the insulator is formed of ceramic epoxy, enamel, or a combination thereof.

4. The endodontic filling instrument of claim 2, wherein the thermocouple of the second metal part and the third metal part is at an end of the heating tip.

5. The endodontic filling instrument of claim 1, wherein the control circuit includes:
    a heater including a resistant tube wire serving as the first metal part of the heating tip, a conductive wire serving as the third metal part, and a thermocouple wire serving as the second metal part;
    a switch for switching power supply applied to the heating tip;
    a heater driver for supplying electric power to the heating tip;
    an amplifier for amplifying a small voltage generated from the thermocouple; and
    a comparator for comparing the amplified voltage with a set temperature.

6. A heating tip of an endodontic instrument for root canal filling, comprising:
    a first metal part serving as a resistant tube;
    a third metal part provided in a tube type and disposed inside the first metal part and configured to supply thermoelectric power and serve as a (−) terminal of a thermocouple;
    a second metal part disposed inside the third metal part in a form of wire and configured to supply the thermoelectric power, check a thermoelectric power (+) terminal, and serve as a (+) terminal of the thermocouple;
    a thermocouple junction in which one end of the second metal part and one end of the third metal part contact each other;
    a first insulator disposed inside the first metal part and enclosing a surface of the third metal part;
    a second insulator disposed inside the third metal part and enclosing a surface of the second metal part;
    a first conductive tube contacting the other end of the second metal part;
    a second conductive tube contacting the other end of the third metal part; and
    a third insulator connected and fixed to the first and second conductive tubes, wherein temperature is detected using the thermoelectric power of the thermocouple of the second and third metal parts.

* * * * *